(12) United States Patent
Brooks et al.

(10) Patent No.: US 10,894,148 B2
(45) Date of Patent: Jan. 19, 2021

(54) BALLOON-MANIPULATING DEVICES, BALLOON CATHETER ASSEMBLIES, AND METHODS THEREOF

(71) Applicant: C. R. Bard, Inc., Murray Hill, NJ (US)

(72) Inventors: Christopher K. Brooks, DeCatur, GA (US); Mark McDermott, Tucker, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 442 days.

(21) Appl. No.: 15/885,476

(22) Filed: Jan. 31, 2018

(65) Prior Publication Data
US 2019/0232028 A1 Aug. 1, 2019

(51) Int. Cl.
*A61M 25/00* (2006.01)
*A61M 25/10* (2013.01)

(52) U.S. Cl.
CPC .... *A61M 25/10184* (2013.11); *A61M 25/007* (2013.01); *A61M 25/1002* (2013.01); *A61M 25/0017* (2013.01); *A61M 2025/1081* (2013.01); *A61M 2025/1084* (2013.01); *A61M 2025/1093* (2013.01); *A61M 2210/1085* (2013.01)

(58) Field of Classification Search
CPC .. A61M 2025/1081; A61M 2025/1084; A61M 2025/1093; A61M 2210/1085; A61M 25/0017; A61M 25/007; A61M 25/1002; A61M 25/10184
See application file for complete search history.

(56) References Cited

U.S. PATENT DOCUMENTS

| | | | |
|---|---|---|---|
| 5,695,479 A | * | 12/1997 | Jagpal ............... A61M 25/0606 604/264 |
| 6,716,200 B2 | | 4/2004 | Bracken et al. |
| 6,716,895 B1 | | 4/2004 | Terry |
| 7,628,784 B2 | | 12/2009 | Diaz et al. |
| 8,034,454 B2 | | 10/2011 | Terry |
| 8,833,268 B2 | | 9/2014 | Shirvinski et al. |

(Continued)

OTHER PUBLICATIONS

PCT/US2019/015902 filed Jan. 30, 2019 International Search Report and Written Opinion dated Apr. 15, 2019.

*Primary Examiner* — Kai H Weng
(74) *Attorney, Agent, or Firm* — Rutan & Tucker LLP

(57) ABSTRACT

A balloon-manipulating device for a balloon catheter, methods of making, and methods of use. The balloon-manipulating device includes a tubular body, a longitudinal hole through a least a portion of the tubular body, one or more balloon-compressing pieces of a sidewall of the tubular body, and one or more balloon-letting through holes through the sidewall. The longitudinal hole may extend from an opened proximal end of the tubular body to at least a distal end portion of the tubular body, and is configured for inserting a balloon-catheter shaft therein. Each of the one or more balloon-compressing pieces is configured for compressing a different portion of an inflated balloon-catheter balloon when the balloon-manipulating device is disposed over the balloon. Each of the one or more balloon-letting through holes is configured for allowing therethrough a different portion of an inflated balloon-catheter balloon when the balloon-manipulating device is disposed over the balloon.

15 Claims, 12 Drawing Sheets

(56) References Cited

U.S. PATENT DOCUMENTS

| | | | |
|---|---|---|---|
| 9,242,075 B2 | 1/2016 | Nishtala et al. | |
| 2002/0177866 A1* | 11/2002 | Weikel | A61B 17/025 606/192 |
| 2006/0195136 A1* | 8/2006 | Yokoyama | A61M 25/104 606/192 |
| 2013/0116655 A1* | 5/2013 | Bacino | A61M 25/1029 604/509 |
| 2016/0346504 A1* | 12/2016 | Arora | A61B 5/205 |

* cited by examiner

BALLOON-MANIPULATING DEVICES, BALLOON CATHETER ASSEMBLIES, AND METHODS THEREOF

BACKGROUND

Urinary catheterization is indicated for surgical and medical patients who require, at least temporarily, assisted bladder voiding. Common indications for catheterizing a patient include acute or chronic urinary retention (which can damage the kidneys), medical procedures that at least temporarily limit the patient's movement, a need for accurate monitoring of input and output (such as in an intensive care unit), benign prostatic hyperplasia, incontinence, or the effects of various surgical interventions involving the bladder or the prostate. Urinary catheterization can be performed with a urinary catheter such as a conventional Foley catheter.

FIG. 1A is a schematic, illustrating a side view of a distal end portion of a conventional Foley catheter 100 with a balloon 120 in an uninflated state. As shown, the conventional Foley catheter 100 includes a shaft 110 terminating in a tip 112 at a distal end of the shaft 110, a drainage hole 114 in a distal end portion of the shaft 110, and a balloon 120 fluidly coupled to an inflation lumen by way of an inflation hole 116 in the shaft 110. FIG. 1B is a schematic illustrating the side view of the distal end portion of the conventional Foley catheter 100 of FIG. 1A with the balloon 120 in an inflated state.

For a urinary catheter such as a Foley catheter, the catheter is introduced into the patient and advanced up the patient's urethra until the distal end portion of the catheter, including the balloon, resides within the bladder. The balloon is then inflated, typically by coupling a syringe to the inflation valve and actuating the syringe to discharge fluid, through the inflation lumen, and into the balloon. While the patient has the catheter in his or her bladder, urine is drained from the bladder. However, there is typically residual urine left in the bladder because of a distance between the drainage hole in the distal end portion of the shaft and a bottom of the bladder. This is shown in FIG. 6A, which illustrates the conventional Foley catheter 100 anchored in a bladder 690 with the balloon 120 in the inflated state and the drainage hole 114 in the distal end portion of the shaft 110 above a volume of urine 696 in the bladder 690. If urine cannot get to a drainage hole in such a catheter, the urine cannot leave the bladder through the catheter. Disclosed herein are balloon-manipulating devices, balloon catheter assemblies, and methods thereof that address the foregoing.

SUMMARY

Disclosed herein is a balloon-manipulating device for a balloon catheter, the balloon-manipulating device including, in some embodiments, a tubular body, a longitudinal hole through a least a portion of the tubular body, one or more balloon-compressing pieces of a sidewall of the tubular body, and one or more balloon-letting through holes through the sidewall of the tubular body. The tubular body includes a proximal end portion and a distal end portion. The longitudinal hole extends from an opened proximal end of the tubular body to at least the distal end portion of the tubular body. The longitudinal hole is configured for inserting a balloon-catheter shaft in the longitudinal hole. Each balloon-compressing piece of the one or more balloon-compressing pieces is configured for compressing a different portion of a balloon-catheter balloon when the balloon-manipulating device is disposed over the balloon and the balloon is in an inflated state thereof. Each balloon-letting through hole of the one or more balloon-letting through holes is configured for allowing therethrough a different portion of a balloon-catheter balloon when the balloon-manipulating device is disposed over the balloon and the balloon is in an inflated state thereof.

In some embodiments, the tubular body is seamless. Such a seamless tubular body is configured to withstand tensile stress imparted to the tubular body when inflating a balloon-catheter balloon under the balloon-manipulating device.

In some embodiments, the tubular body includes a closed distal end, thereby forming a balloon-manipulating cap configured for inserting a balloon-catheter shaft therein.

In some embodiments, the tubular body includes an opened distal end, thereby forming a balloon-manipulating sleeve configured for inserting a balloon-catheter shaft therethrough.

In some embodiments, the tubular body includes one or more tabs, one or more cutouts, or a combination thereof. Each tab of the one or more tabs independently extends from the distal end portion or the proximal end portion of the tubular body. Each cutout of the one or more cutouts independently is in the distal end portion or the proximal end portion of the tubular body.

In some embodiments, the balloon-manipulating device includes n-fold rotational symmetry about a longitudinal axis of the balloon-manipulating device.

In some embodiments, the tubular body includes an opened distal end, thereby forming a balloon-manipulating sleeve configured for inserting a balloon-catheter shaft therethrough. The tubular body includes a pair of tabs and a pair of cutouts. Each tab of the pair of tabs extends from an opposite side of the distal end portion of the tubular body. Each cutout of the pair of cutouts is in an opposite side of the proximal end portion of the tubular body. The tubular body is seamless to withstand tensile stress imparted to the tubular body when inflating a balloon-catheter balloon under the balloon-manipulating sleeve. The balloon-manipulating sleeve includes 2-fold rotational symmetry about a longitudinal axis of the balloon-manipulating sleeve.

Also disclosed herein is a balloon catheter assembly including, in some embodiments, a balloon catheter and a balloon-manipulating device. The balloon catheter includes one or more primary drainage apertures in a distal end portion of a shaft of the balloon catheter, one or more secondary drainage apertures in the distal end portion of the shaft, and a balloon. The one or more secondary drainage apertures are closer to a proximal end portion of the shaft than the one or more primary drainage apertures. The balloon is coupled to the shaft between the primary and secondary drainage apertures. The balloon is fluidly coupled to an inflation lumen configured for inflating the balloon, the inflation lumen extending through a length of the shaft. The balloon-manipulating device includes a tubular body disposed over the balloon, one or more balloon-compressing pieces of a sidewall of the tubular body, and one or more balloon-letting through holes through the sidewall of the tubular body. The tubular body includes a proximal end portion adjacent the one or more primary drainage apertures and a distal end portion adjacent the one or more secondary drainage apertures. Each balloon-compressing piece of the one or more balloon-compressing pieces is configured for compressing a different portion of the balloon when the balloon is in an inflated state thereof. Each balloon-letting through hole of the one or more balloon-letting through holes is configured for allowing therethrough a different portion of the balloon when the balloon is in the inflated state thereof.

In some embodiments, each different portion of the balloon compressed by the one or more balloon-compressing pieces forms a channel when the balloon is in the inflated state. Each different portion of the balloon let through the one or more balloon-letting through holes forms a balloon lobe when the balloon is in the inflated state. One or more balloon lobes are configured to anchor the balloon catheter assembly in a bladder of a patient. One or more channels are configured to transport residual urine from the bladder, through a bladder neck, through a portion of a urethra, and to the one or more secondary drainage apertures for drainage of the residual urine.

In some embodiments, the balloon catheter assembly includes a one-to-one-to-one correspondence of the one or more secondary drainage apertures, the one or more balloon-compressing pieces, and the one or more balloon-letting through holes.

In some embodiments, the tubular body is seamless. Such a seamless tubular body is configured to withstand tensile stress imparted to the tubular body when the balloon is in the inflated state.

In some embodiments, the tubular body includes an opened proximal end and a closed distal end, thereby forming a balloon-manipulating cap. The balloon-manipulating cap includes one or more sidewall through holes in the distal end portion of the tubular body configured to align with the one or more primary drainage apertures.

In some embodiments, the tubular body includes an opened proximal end and an opened distal end, thereby forming a balloon-manipulating sleeve.

In some embodiments, the tubular body includes one or more tabs, one or more cutouts, or a combination thereof. Each tab of the one or more tabs independently extends from the distal end portion or the proximal end portion of the tubular body. Each cutout of the one or more cutouts independently is in the distal end portion or the proximal end portion of the tubular body.

In some embodiments, the one or more tabs are circumferentially arranged around the distal end portion of the tubular body, and the one or more cutouts are circumferentially arranged around the proximal end portion of the tubular body. The one or more tabs alternate with the one or more primary drainage apertures, and the one or more cutouts align with the one or more secondary drainage apertures.

In some embodiments, the tubular body includes an opened proximal end and an opened distal end, thereby forming a balloon-manipulating sleeve. The tubular body includes a pair of tabs extending from the distal end portion of the tubular body, and the tubular body includes a pair of cutouts in the proximal end portion of the tubular body.

In some embodiments, the balloon-manipulating device includes $C_2$ symmetry about a longitudinal axis of the balloon-manipulating device.

In some embodiments, the pair of tabs are circumferentially arranged around the distal end portion of the tubular body to include one primary drainage aperture between the pair of tabs or alternate with two primary drainage apertures. The pair of cutouts are circumferentially arranged around the proximal end portion of the tubular body to align with one or two secondary drainage apertures.

Also disclosed herein is a balloon catheter assembly including, in some embodiments, a balloon catheter and a balloon-manipulating sleeve. The balloon catheter includes one or two primary drainage apertures in a distal end portion of a shaft of the balloon catheter, one or two secondary drainage apertures in the distal end portion of the shaft, and a balloon. The one or two secondary drainage apertures are closer to a proximal end portion of the shaft than the one or two primary drainage apertures. The balloon is coupled to the shaft between the primary and secondary drainage apertures. The balloon is fluidly coupled to an inflation lumen configured for inflating the balloon, the inflation lumen extending through a length of the shaft. The balloon-manipulating sleeve includes a tubular body disposed over the balloon, one or two balloon-compressing pieces of a sidewall of the tubular body, and one or two balloon-letting through holes through the sidewall of the tubular body. The tubular body includes a proximal end portion adjacent the one or two primary drainage apertures and a distal end portion adjacent the one or two secondary drainage apertures. Each balloon-compressing piece of the one or two balloon-compressing pieces is configured for compressing a different portion of the balloon to form a corresponding channel when the balloon is in an inflated state thereof. Each balloon-letting through hole of the one or two balloon-letting through holes is configured for allowing therethrough a different portion of the balloon to form a corresponding balloon lobe when the balloon is in the inflated state thereof. One or two balloon lobes are configured to anchor the balloon catheter assembly in a bladder of a patient. One or two channels are configured to transport residual urine from the bladder, through a bladder neck, through a portion of a urethra, and to the one or two secondary drainage apertures for drainage of the residual urine while the balloon catheter assembly is anchored in the bladder of the patient by the one or two balloon lobes.

In some embodiments, the balloon catheter assembly includes one primary drainage aperture and one secondary drainage aperture in the distal end portion of the shaft, one balloon-compressing piece of the sidewall of the tubular body, and one balloon-letting through hole through the sidewall of the tubular body.

In some embodiments, the balloon catheter assembly includes one primary drainage aperture and two secondary drainage apertures in the distal end portion of the shaft, two balloon-compressing pieces of the sidewall of the tubular body, and two balloon-letting through holes through the sidewall of the tubular body.

DRAWINGS

DESCRIPTION

Figure 1A:
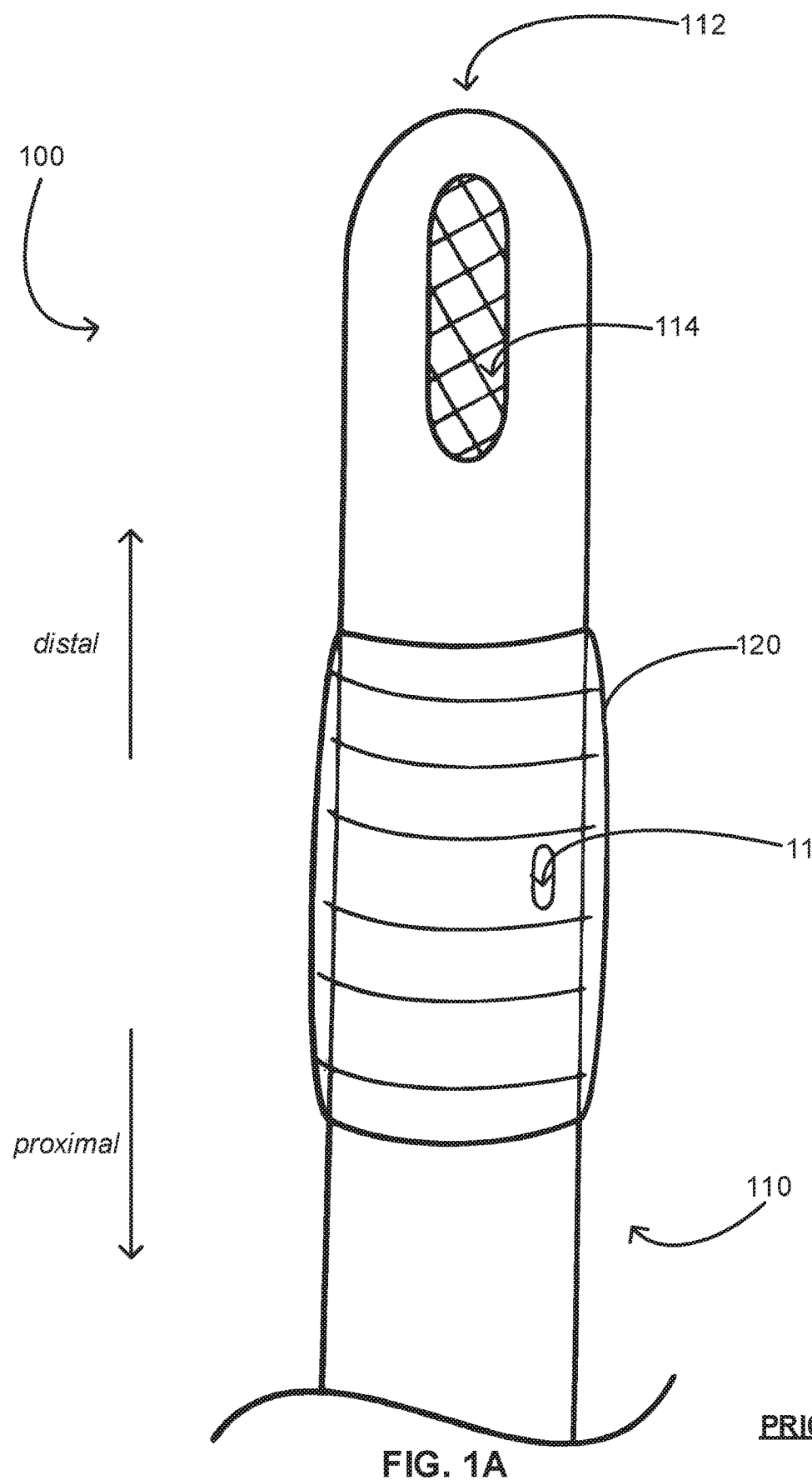
FIG. 1A is a schematic illustrating a side view of a distal end portion of a conventional Foley catheter with a balloon in an uninflated state.
Figure 1B:
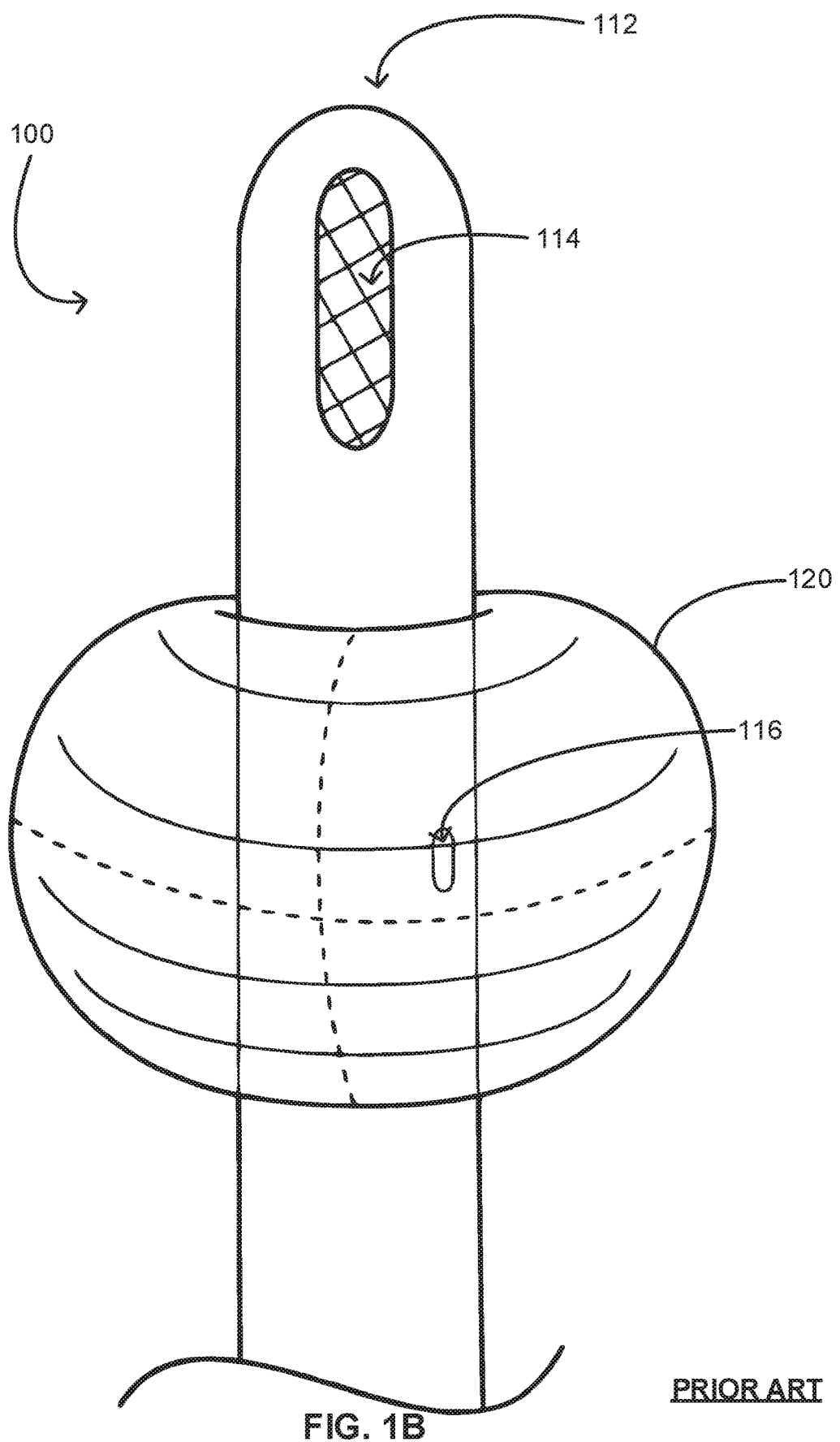
FIG. 1B is a schematic illustrating the side view of the distal end portion of the conventional Foley catheter of FIG. 1A with the balloon in an inflated state.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Again, for a urinary catheter such as a Foley catheter, while a patient has the catheter in his or her bladder, urine is drained from the bladder. However, there is typically residual urine left over because of a distance between drainage holes of the catheter and a bottom of the bladder. If urine cannot get to the drainage holes, the urine cannot leave the bladder through the catheter. Disclosed herein are balloon-manipulating devices, balloon catheter assemblies, and methods thereof that address the foregoing.

For example, a balloon catheter assembly is disclosed including, in some embodiments, a balloon catheter and a balloon-manipulating device. The balloon catheter includes one or more primary drainage apertures in a distal end portion of a shaft of the balloon catheter, one or more secondary drainage apertures in the distal end portion of the shaft, and a balloon. The one or more secondary drainage apertures are closer to a proximal end portion of the shaft than the one or more primary drainage apertures. The balloon is coupled to the shaft between the primary and secondary drainage apertures. The balloon is fluidly coupled to an inflation lumen configured for inflating the balloon, the inflation lumen extending through a length of the shaft. The balloon-manipulating device includes a tubular body disposed over the balloon, one or more balloon-compressing pieces of a sidewall of the tubular body, and one or more balloon-letting through holes through the sidewall of the tubular body. The tubular body includes a proximal end portion adjacent the one or more primary drainage apertures and a distal end portion adjacent the one or more secondary drainage apertures. Each balloon-compressing piece of the one or more balloon-compressing pieces is configured for compressing a different portion of the balloon to form a corresponding channel when the balloon is in an inflated state thereof. Each balloon-letting through hole of the one or more balloon-letting through holes is configured for allowing therethrough a different portion of the balloon to form a corresponding balloon lobe when the balloon is in the inflated state thereof. One or more channels are configured to transport residual urine from the patient's bladder, through the bladder neck and a portion of the urethra, and to the one or more secondary drainage apertures for drainage of the residual urine while the balloon catheter assembly is anchored in the bladder of the patient by the one or more balloon lobes.

Figure 2:
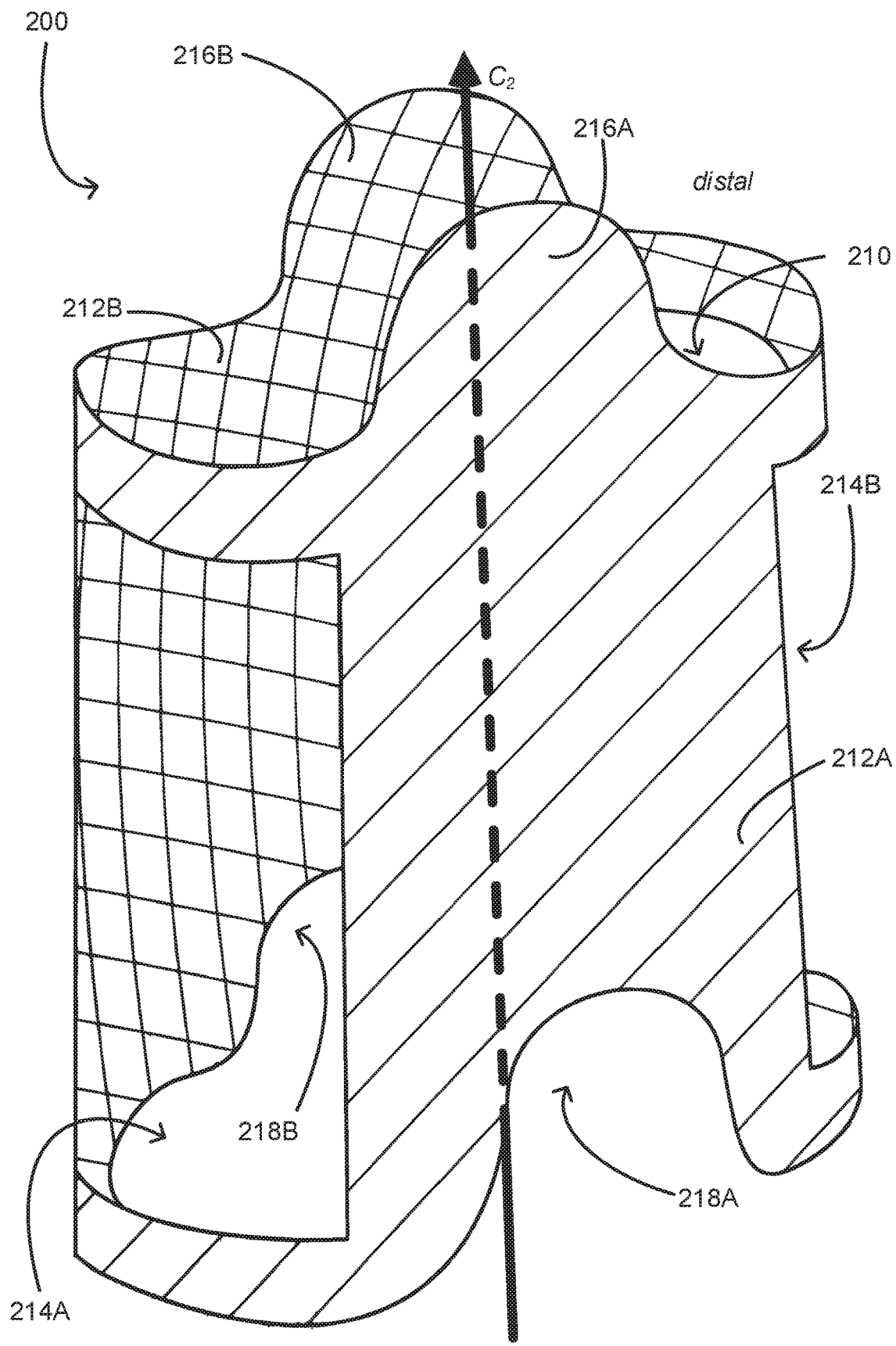
FIG. 2 is schematic illustrating a balloon-manipulating device for a balloon of a balloon catheter in accordance with some embodiments.

FIG. 2 is schematic illustrating a balloon-manipulating device 200 for a balloon of a balloon catheter in accordance with some embodiments. As shown, the balloon-manipulating device 200 includes a body 210, one or more balloon-compressing pieces 212, and one or more balloon-letting through holes 214. Since the embodiment of the balloon-manipulating device 200 shown in FIG. 2 includes two balloon-compressing pieces 212, each balloon-compressing piece is individually identified as balloon-compressing piece 212A and balloon-compressing piece 212B. Likewise, since the embodiment of the balloon-manipulating device 200 shown in FIG. 2 includes two balloon-letting through holes 214, each balloon-letting through hole is individually identified as balloon-letting through hole 214A and balloon-letting through hole 214B. Depending upon embodiment of the balloon-manipulating device 200, the balloon-manipulating device 200 includes one or more tabs 216 such as tab 216A and tab 216B, as well as one or more notches 218 such as notch 218A and notch 218B.

The body 210 of the balloon-manipulating device 200 can be tubular, and the tubular body 210 includes a proximal end portion and a distal end portion. A longitudinal hole can extend through a least a portion of the tubular body 210 such as from an opened proximal end of the tubular body 210 to at least the distal end portion of the tubular body 210. The longitudinal hole is sized and configured for inserting a balloon-catheter shaft in the longitudinal hole. The body 210 of the balloon-manipulating device 200 remains flush against the balloon-catheter shaft, thereby allowing for smooth insertion of the balloon catheter into a patient.

Figure 4A:
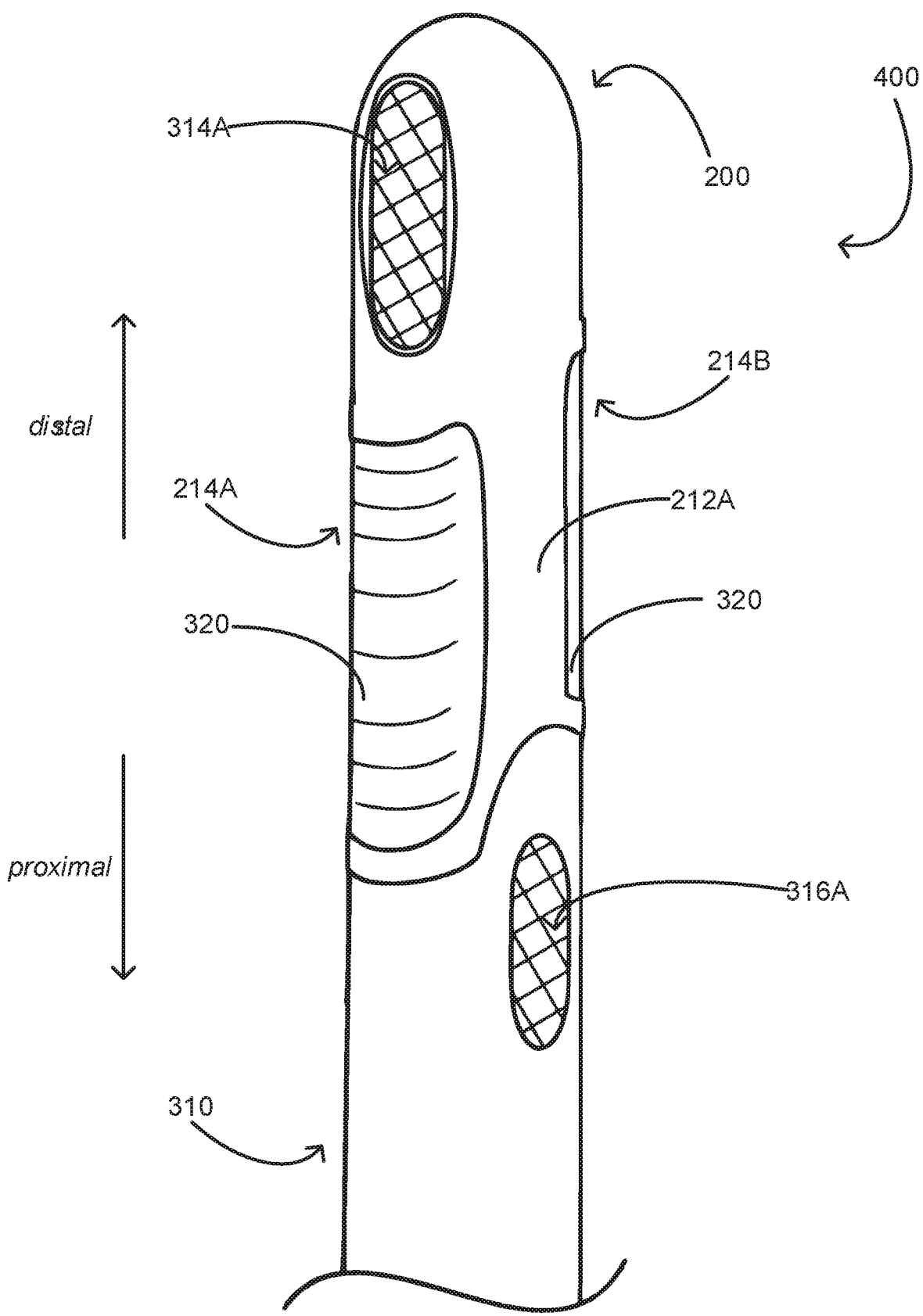
FIG. 4A is a schematic illustrating a first side view of a distal end portion of a balloon catheter assembly with a balloon-shaping cap disposed over a balloon in an uninflated state in accordance with some embodiments.
Figure 4B:
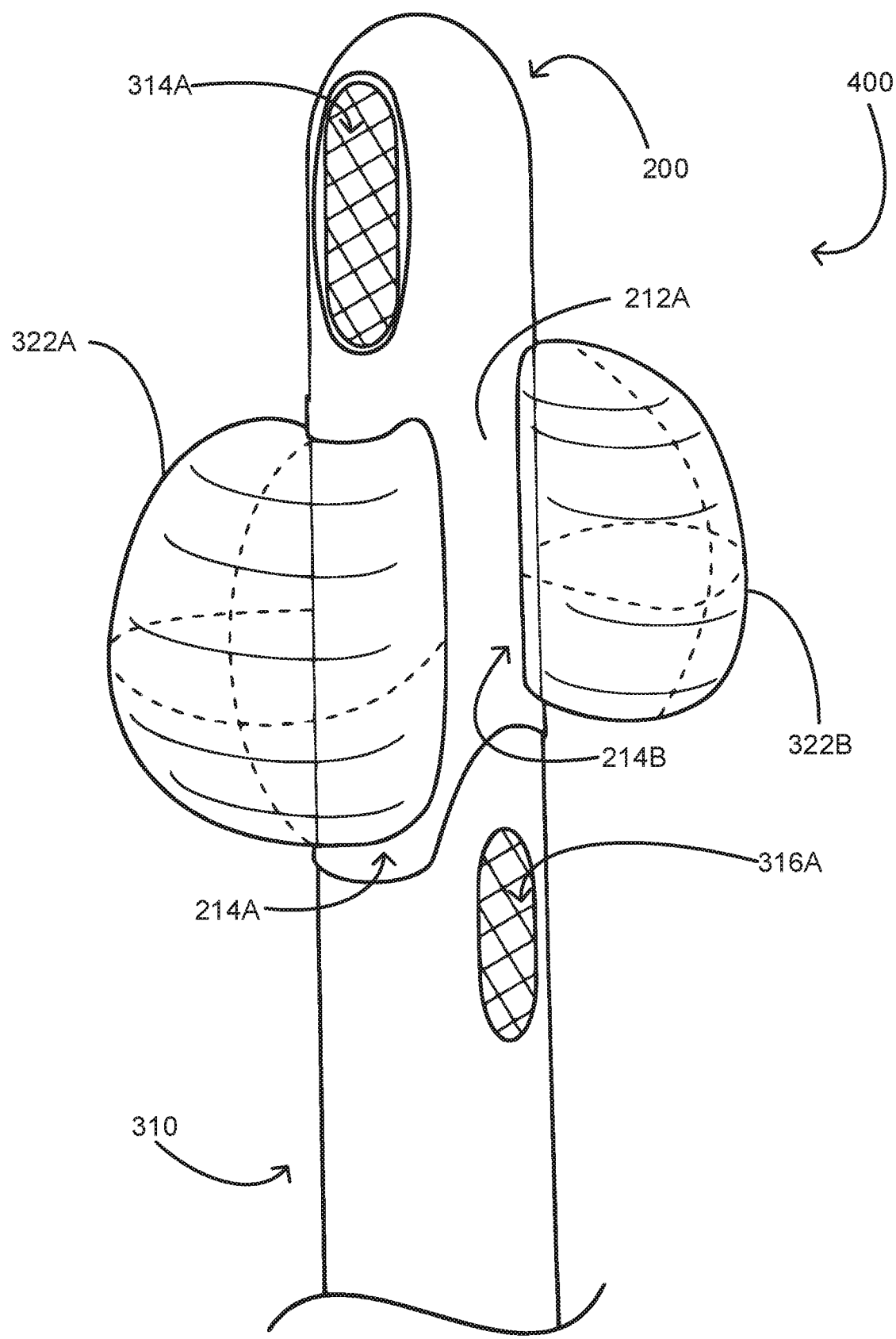
FIG. 4B is a schematic illustrating the first side view of the distal end portion of the balloon catheter assembly of FIG. 4A with the balloon-shaping cap disposed over the balloon in an inflated state.

The tubular body 210 can include a closed distal end, thereby forming a balloon-manipulating cap. The longitudinal hole, which extends from the opened proximal end to the closed distal end of the tubular body, is sized and configured for inserting a balloon-catheter shaft therein. Such a cap, which is shown in detail in FIGS. 4A and 4B, provides a stop by way of the closed distal end, thereby preventing over insertion of the balloon-catheter shaft in the longitudinal hole. While this provides consistent longitudinal alignment of the balloon-manipulating cap over a balloon of a balloon catheter, circumferential alignment of any primary drainage apertures (see primary drainage apertures 314 of FIGS. 4A and 4B) of the balloon-catheter shaft with corresponding sidewall through holes in the distal end portion of the tubular body allows for drainage therethrough. As such, the balloon-manipulating cap includes one or more sidewall through holes in the distal end portion of the tubular body 210 configured to respectively align with one or more primary drainage apertures of the balloon-catheter shaft.

The tubular body 210 can include an opened distal end, thereby forming a balloon-manipulating sleeve. The longitudinal hole, which extends from the opened proximal end to the opened distal end of the tubular body, is sized and configured for inserting a balloon-catheter shaft therethrough. Such a sleeve, which is shown in detail in FIG. 2 and FIGS. 3A-3D, obviates the sidewall through holes in the distal end portion of the tubular body of the balloon-manipulating cap, as well as any associated circumferential alignment.

Whether the balloon-manipulating device 200 is a cap or a sleeve, the balloon-manipulating device 200 includes the one or more balloon-compressing pieces 212 and the one or more balloon-letting through holes 214. Each balloon-compressing piece of the one or more balloon-compressing pieces 212 is configured for compressing or holding flush against the balloon-catheter shaft a different portion of a balloon-catheter balloon when the balloon-manipulating device 200 is disposed over the balloon and the balloon is in an inflated state thereof. Each balloon-letting through hole of the one or more balloon-letting through holes 214 is configured for allowing therethrough a different portion of the balloon-catheter balloon when the balloon-manipulating device 200 is disposed over the balloon and the balloon is in an inflated state thereof (See, for example, FIGS. 3C, 3D, and 4B.)

As exemplified by the balloon-compressing piece 212A and the balloon-compressing piece 212B of FIG. 2, each balloon-compressing piece of the one or more balloon-compressing pieces 212 is formed of at least a portion of sidewall of the tubular body 210. As exemplified by the balloon-letting through hole 214A and the balloon-letting through hole 214B of FIG. 2, each balloon-letting through hole of the one or more balloon-letting through hole 214 is formed in the sidewall of the tubular body 210. There is no particular limit on the number of balloon-compressing pieces 212 or balloon-letting through holes 214 in the balloon-manipulating device 200; however, the balloon-compressing pieces 212 and the balloon-letting through holes 214 are present in the balloon-manipulating device 200 in a one-to-one correspondence. That is, for every balloon-letting through hole formed in the sidewall of the tubular body 210, a balloon-compressing piece is also formed in the sidewall of the tubular body 210.

Whether the balloon-manipulating device 200 is a cap or a sleeve, the tubular body 210 can include one or more tabs 216, one or more cutouts 218, or a combination thereof. Such tabs and cutouts can be useful for pulling the balloon-manipulating device 200 onto a balloon-catheter shaft, removing the balloon-manipulating device from the balloon-catheter shaft, or both. No particular arrangement is required of the one or more tabs 216 to any other tab, the one or more cutouts 218 to any other cutout, or the one or more tabs 216 and the one or more cutouts 218 among each other. That said, certain arrangements do have certain advantages. As shown in FIG. 2, for example, longitudinal alignment of an opposing pair of cutouts 218 (e.g., cutouts 218A and 218B) in a first end portion (e.g., proximal end portion) of the balloon-manipulating device 200 with an opposing pair tabs 216 (e.g., tabs 216A and 216B) in a second end portion (e.g., distal end portion) of the balloon-manipulating device 200 facilitates manufacturing in that a single cut to a tubular extrusion simultaneously forms both the opposing pair of cutouts 218 in the first end portion and the opposing pair tabs 216 in the second end portion. Manufacturing in this way reduces material waste and, therefore, material costs.

Notwithstanding the foregoing, each tab of the one or more tabs 216 independently extends from the distal end portion or the proximal end portion of the tubular body 210. For example, the one or more tabs 216 can be circumferentially arranged (e.g., equidistant from each other) around the distal end portion of the tubular body 210 as shown in FIGS. 2 and 3A-3D. FIG. 2 also shows the foregoing opposing pair of tabs 216 including a first tab 216A and a second tab 216B extending from opposite sides of the distal end portion of the tubular body 210; however, there is no particular limit on the number of tabs 216, the end portions of the tubular body 210 from which the one or more tabs 216 extend, or arrangements of the one or more tabs with respect to each other about the end portions of the tubular body 210.

Further, each cutout of the one or more cutouts 218 is independently in, or cut from, the distal end portion or the proximal end portion of the tubular body 210. For example, the one or more cutouts 218 can be circumferentially arranged (e.g., equidistant from each other) around the proximal end portion of the tubular body 210 as shown in FIGS. 2 and 3A-3D. FIG. 2 also shows the foregoing opposing pair of cutouts 218 including a first cutout 218A and a second cutout 218B in opposite sides of the proximal end portion of the tubular body 210; however, there is no particular limit on the number of cutouts 218, the end portions of the tubular body 210 from which the one or more cutouts 218 are cut, or arrangements of the one or more cutouts 218 with respect to each other about the end portions of the tubular body 210.

Whether the balloon-manipulating device 200 is a cap or a sleeve, the tubular body 210 can be seamless. Again, the balloon-manipulating device 200 can be cut from a tubular extrusion, which can be a seamless tubular extrusion. Such a seamless tubular body obviates any weak point or points of failure along a length of the tubular body 210. As such, the tubular body 210 is configured to withstand tensile stress imparted to the tubular body 210 when inflating a balloon-catheter balloon under the balloon-manipulating device 200 or while the balloon is partially or fully inflated.

The balloon-manipulating device 200 including the one or more balloon-compressing pieces 212, the one or more balloon-letting through holes 214, and, if present, any of the one or more tabs 216 or the one or more cutouts 218 can have n-fold rotational symmetry, or $C_n$ symmetry, about a longitudinal axis of the balloon-manipulating device 200. As shown in FIG. 2, for example, the balloon-manipulating device 200 has 2-fold rotational symmetry, or $C_2$ symmetry, about the longitudinal axis of the balloon-manipulating device 200. As alluded to in FIG. 5C, for example, a balloon-manipulating device 200 having three equally spaced balloon-compressing pieces 512 (e.g., balloon-compressing pieces 512D, 512E, and 512F) alternating with three equally spaced balloon-letting through holes 514 (not shown) can have 3-fold rotational symmetry, or $C_3$ symmetry, about the longitudinal axis of the balloon-manipulating device 200. Likewise, as alluded to in FIG. 5D, for example, a balloon-manipulating device 200 having four equally spaced balloon-compressing pieces 512 alternating with four equally spaced balloon-letting through holes 514 (not shown) can have 4-fold rotational symmetry, or $C_4$ symmetry, about the longitudinal axis of the balloon-manipulating device 200.

The balloon-manipulating device 200 can be made of any material that performs the functions already set forth. As such, the balloon-manipulating device 200 can be constructed from a variety of materials including, but not limited to, a polymeric material such as polytetrafluoroethylene ("PTFE") or expanded PTFE ("ePTFE"). In some embodiments, the balloon-manipulating device 200 can be reinforced with one or more other materials including, but not limited to, an embedded material such as a braided material. In some embodiments, the balloon-manipulating device 200 is formed of a rubber latex the same as or similar to that used to construct the balloon-catheter shaft. In such cases, the rubber latex balloon-manipulating device 200 might need to be stronger or stiffer than the same or similar material of the balloon-catheter balloon so that it performs the functions already set forth.

The material of the balloon-manipulating device 200 is of sufficient strength to withstand forces associated with inflating the balloon-catheter balloon without deflecting or failing. A thickness of the balloon-manipulating device 200 is optimized to minimize an overall diameter of the balloon-catheter shaft while providing the sufficient strength to withstand the forces associated with inflating the balloon-catheter balloon. In addition to being seamless, the balloon-manipulating device 200 can be manufactured such that there are no areas of the balloon-manipulating device 200 that are sharp enough to puncture the balloon-catheter balloon.

Figure 3A:
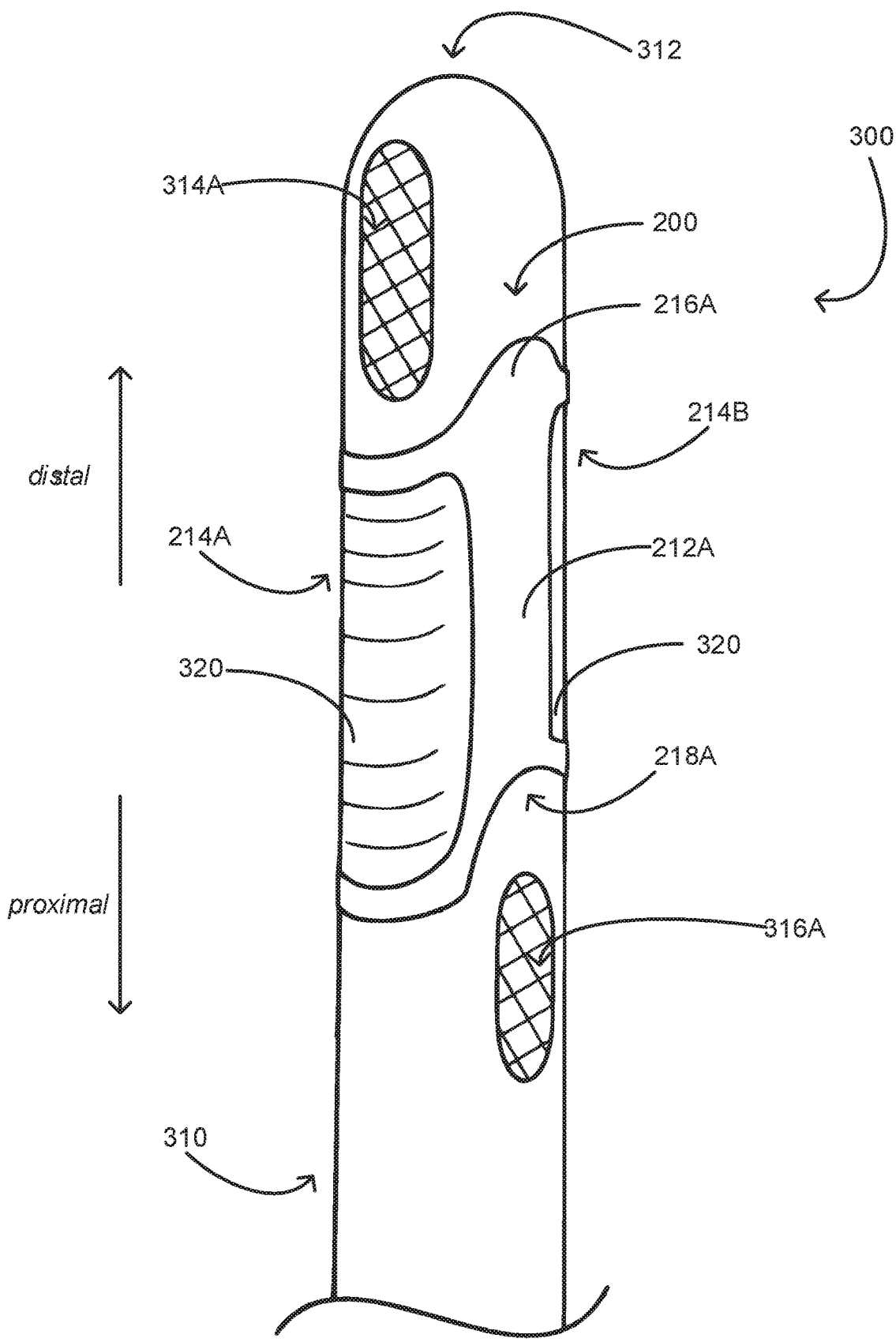
FIG. 3A is a schematic illustrating a first side view of a distal end portion of a balloon catheter assembly with a balloon-shaping sleeve disposed over a balloon in an uninflated state in accordance with some embodiments.
Figure 3B:
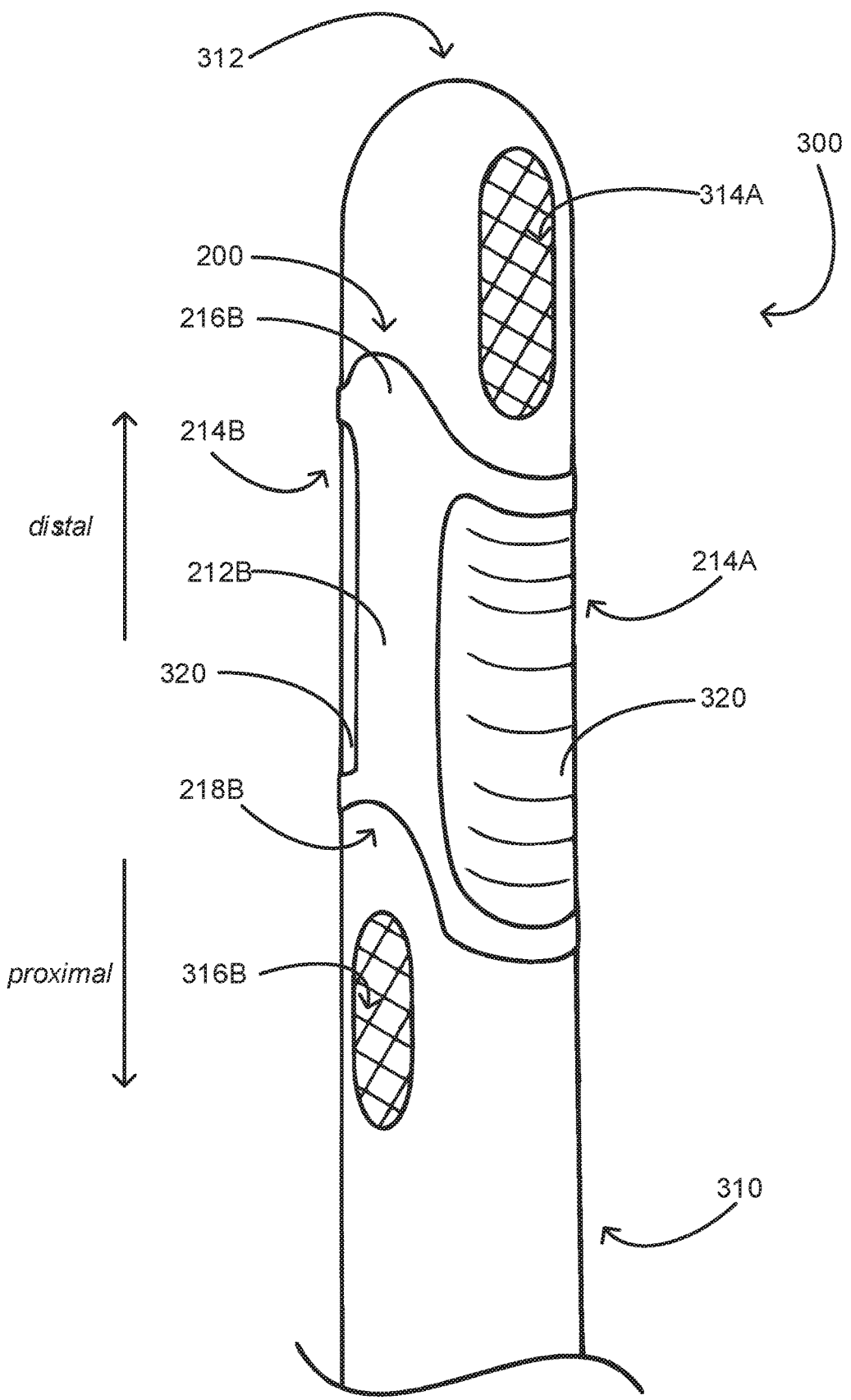
FIG. 3B is a schematic illustrating a second side view of the distal end portion of the balloon catheter assembly of FIG. 3A with the balloon-shaping sleeve disposed over the balloon in the uninflated state.

FIG. 3A is a schematic illustrating a first side view of a distal end portion of a balloon catheter assembly 300 with the balloon-manipulating device 200 configured as a balloon-shaping sleeve disposed over a balloon 320 in an uninflated state in accordance with some embodiments. FIG. 3B is a schematic illustrating a second side view of the distal end portion of the balloon catheter assembly 300 of FIG. 3A with the balloon-shaping sleeve disposed over the balloon 320 in the uninflated state.

As shown, the balloon catheter assembly 300 includes a shaft 310 of a balloon catheter terminating in a tip 312 at a distal end of the shaft 310, one or more primary drainage apertures 314 exemplified by the primary drainage aperture 314A in a distal end portion of the shaft 310, and one or more secondary drainage apertures 316 also in the distal end portion of the shaft 310. The one or more secondary drainage apertures 316 are exemplified by a first secondary drainage aperture 316A in FIG. 3A and a second secondary drainage aperture 316B in FIG. 3B. The one or more secondary drainage apertures 316 can be in various positions along the shaft 310 advantageous to urine drainage. For example, the one or more secondary drainage apertures 316 can be disposed more distally or proximally than illustrated in FIGS. 3A and 3B. However, the one or more secondary drainage apertures 316 are closer to a proximal end portion of the shaft 310 than the one or more primary drainage apertures 314. The balloon 320 is coupled to the shaft 310 between the primary drainage apertures 314 and the secondary drainage apertures 316. While not expressly shown in FIGS. 3A and 3B, the balloon 320 is fluidly coupled to an inflation lumen extending through a length of the shaft 310 for inflating the balloon 320 by way of an inflation hole in the shaft 310. The balloon 320 can be inflated by infusing a substance such as sterile water into an inflation port at the proximal end of the balloon catheter assembly catheter 300 (not shown).

While the shaft 310 of the balloon catheter assembly 300 of FIGS. 3A and 3B is shown with one primary drainage aperture 314A and two secondary drainage apertures 316A in 316B in the distal end portion of the shaft 310, the balloon catheter assembly 300 is not limited to the foregoing number of primary and secondary drainage apertures or the arrangement thereof. The balloon catheter assembly 300 includes at least the one primary drainage aperture 314A in the shaft 310, but the balloon catheter assembly 300 can further include one or more additional primary drainage apertures 314 resulting in, for example, a total of two, three, or four primary drainage apertures 314 in the shaft 310. Such primary drainage apertures 314 can be equally spaced around a circumference of the distal end portion of the shaft 310. Likewise, the balloon catheter assembly 300 includes at least one secondary drainage aperture in the shaft 310 such as the secondary drainage aperture 316A, but the balloon catheter assembly 300 can further include one or more additional secondary drainage apertures 316 resulting in, for example, a total of two, three, or four secondary drainage apertures 316 in the shaft 310. As exemplified by the two secondary drainage apertures 316A in 316B, such secondary drainage apertures 316 can be equally spaced around a circumference of the distal end portion of the shaft 310. The one or more primary drainage apertures 314 and the one or more secondary drainage apertures 316 can be longitudinally aligned with each other on the shaft 310, offset from each other on the shaft 310, or a combination thereof in embodiments including at least two primary drainage apertures 314 or at least two secondary drainage apertures 316. For example, FIGS. 3A and 3B show the primary drainage aperture 314A longitudinally offset from the two secondary drainage apertures 316A in 316B, but the primary drainage aperture 314A could be longitudinally aligned with the secondary drainage aperture 316A and offset from the secondary drainage aperture 316B.

Burnishing or polishing any of the primary or secondary drainage apertures 314 or 316 smooths the drainage apertures and minimizes tissue damage during catheter insertion and withdrawal.

As shown, the balloon catheter assembly 300 further includes the balloon-manipulating device 200, which can be configured as a balloon-shaping sleeve having an open-ended tubular body 210 (see FIG. 2) with an opened proximal end and an opened distal end. The balloon-shaping sleeve can be disposed over the balloon 320 such that a proximal end portion of the tubular body 210 is adjacent the one or more primary drainage apertures 314 and a distal end portion of the tubular body 210 is adjacent the one or more secondary drainage apertures 316.

The balloon-shaping sleeve can include one or more tabs 216 extending from the tubular body 210, one or more cutouts 218 in or, otherwise, cut out from, the tubular body 210, or a combination thereof. As exemplified by the tabs 216A and 216B, each tab of the one or more tabs 216 can independently extend from the distal end portion of the tubular body 210. As further exemplified by the tabs 216A and 216B, two or more of the tabs 216 can be circumferentially arranged (e.g., equally spaced or equidistant from each other) around the distal end portion of the tubular body 210. Circumferential arrangement of the two or more tabs 216 around the distal end portion of the tubular body 210 allows the two or more tabs 216 to alternate with the one or more primary drainage apertures 314. Depending upon how far the two or more tabs 216 extend toward the tip 312 of the shaft 310, the two or more tabs 216 can appear as staggered with the one or more primary drainage apertures 314 as shown in FIGS. 3A and 3B. As exemplified by the cutouts 218A and 218B, each cutout of the one or more cutouts 218 can independently be in the proximal end portion of the tubular body 210. As further exemplified by the cutouts 218A and 218B, two or more of the cutouts 218 can be circumferentially arranged (e.g., equally spaced or equidistant from each other) around the proximal end portion of the tubular body 210. Circumferential arrangement of the two or more cutouts 218 around the proximal end portion of the tubular body 210 allows the two or more cutouts 218 to align with the one or more secondary drainage apertures 316 as shown in FIGS. 3A and 3B.

Figure 3C:
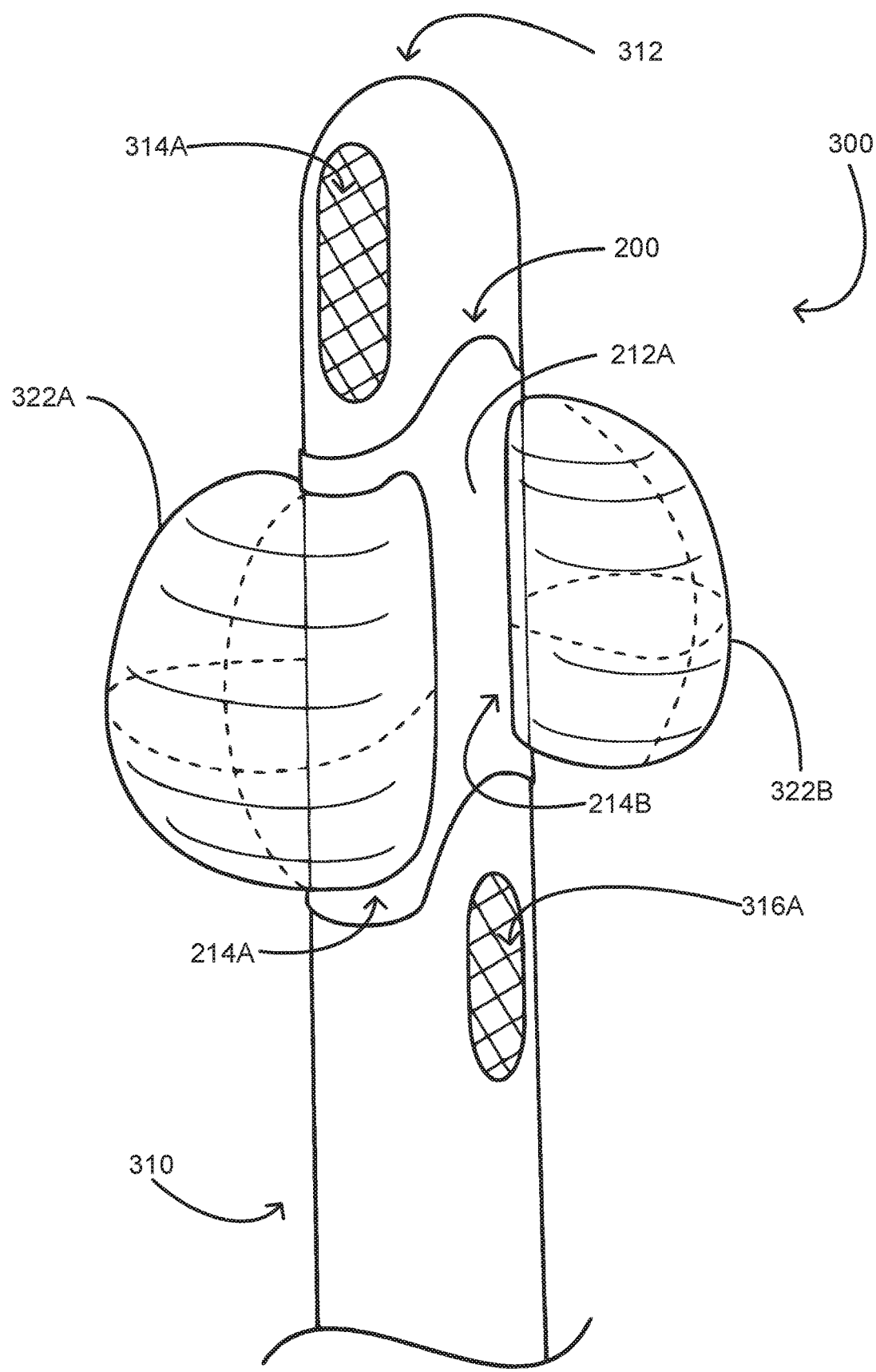
FIG. 3C is a schematic illustrating the first side view of the distal end portion of the balloon catheter assembly of FIG. 3A with the balloon-shaping sleeve disposed over the balloon in an inflated state.
Figure 3D:
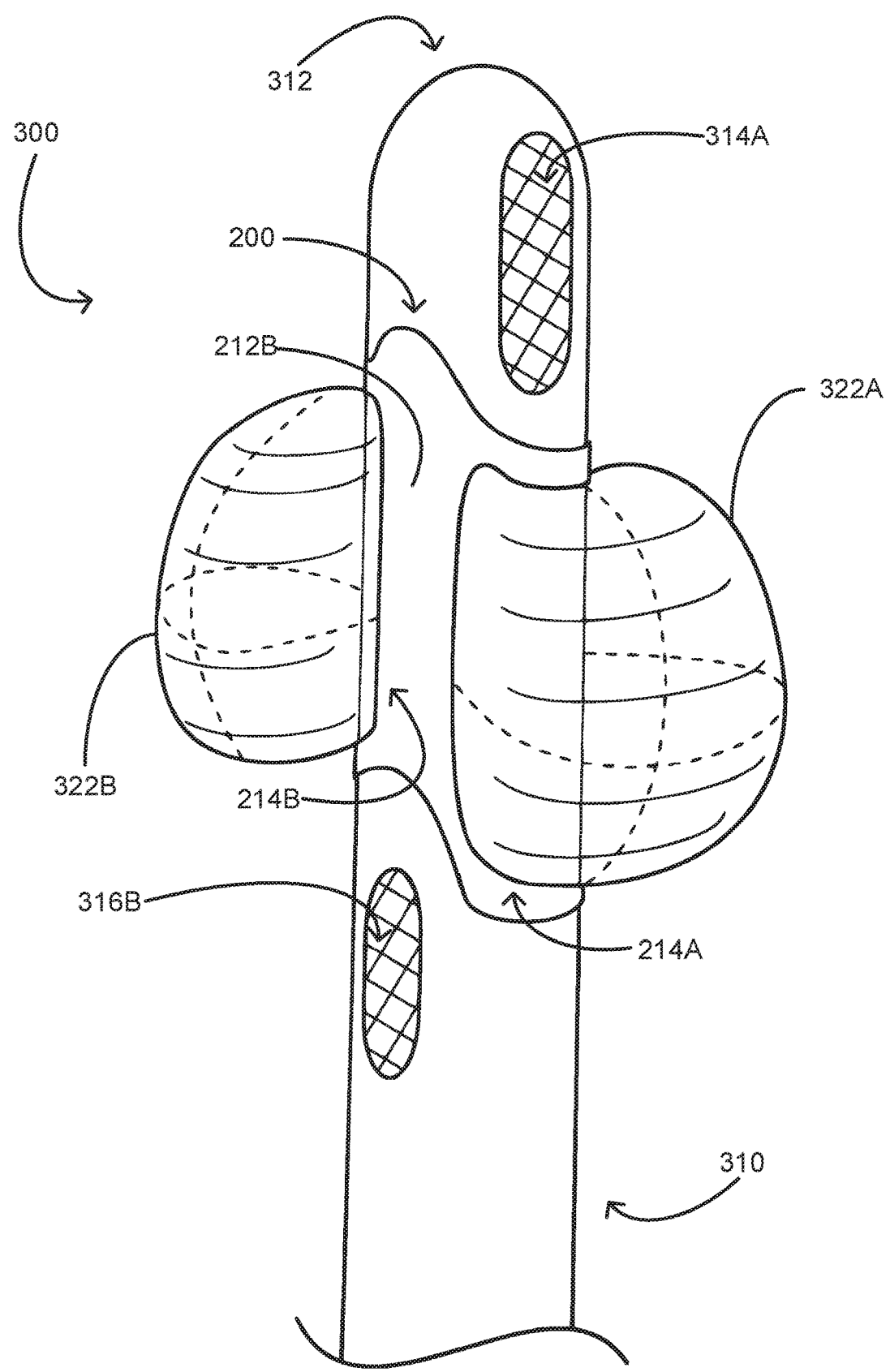
FIG. 3D is a schematic illustrating the second side view of the distal end portion of the balloon catheter assembly of FIG. 3B with the balloon-shaping sleeve disposed over the balloon in an inflated state.

FIG. 3C is a schematic illustrating the first side view of the distal end portion of the balloon catheter assembly 300 of FIG. 3A with the balloon-manipulating device 200 configured as the balloon-shaping sleeve disposed over the balloon 320 in an inflated state. FIG. 3D is a schematic illustrating the second side view of the distal end portion of the balloon catheter assembly 300 of FIG. 3B with the balloon-shaping sleeve disposed over the balloon 320 in an inflated state.

As shown, the balloon-manipulating device 200 of the balloon catheter assembly 300 configured as the balloon-shaping sleeve of FIGS. 3A-3D further includes one or more balloon-compressing pieces 212 of a sidewall of the tubular body 210 and one or more balloon-letting through holes 214 through the sidewall of the tubular body 210. The one or more balloon-compressing pieces 212 are exemplified by the balloon-compressing pieces 212A and 212B, and the one or more balloon-letting through holes 214 are exemplified by the balloon letting though holes 214A and 214B. As described in reference to FIGS. 5A-5D, there is no particular limit on the number or arrangement of the balloon-compressing pieces 212 or the balloon-letting through holes 214.

Each balloon-compressing piece of the one or more balloon-compressing pieces 212 is configured for compressing a different portion of the balloon 320 when the balloon 320 is being inflated or in an inflated state thereof. Each different portion of the balloon 320 compressed by the one or more balloon-compressing pieces 212 forms a channel when the balloon 320 is being inflated or in an inflated state thereof. The one or more channels are coextensive with the one or more balloon-compressing pieces 212 and lie between the one or more balloon-letting through holes 214 or one or more balloon lobes 322 when the balloon 320 is being inflated or in an inflated state thereof. The one or more channels are configured to transport residual urine from a patient's bladder (i.e., urine not drained or capable of being drained from the patient's bladder by the primary drainage apertures 314), through the bladder neck, through a portion of the urethra, and to the one or more secondary drainage apertures 316 for drainage of the residual urine. (See FIG. 5B.) As such, the balloon catheter assembly 300 is configured such that each channel of the one or more channels is longitudinally aligned with a secondary drainage hole of the one or more secondary drainage holes 316.

Each balloon-letting through hole of the one or more balloon-letting through holes 214 is configured for allowing therethrough a different portion of the balloon 320 when the balloon 320 is being inflated or in the inflated state thereof. Each different portion of the balloon 320 let through the one or more balloon-letting through holes 214 forms a balloon lobe such as balloon lobes 322A and 322B when the balloon 320 is being inflated or in an inflated state thereof. The one or more balloon lobes 322 flank the one or more channels or, otherwise, form the one or more channels with the balloon-compressing pieces 212, when the balloon 320 is being inflated or in an inflated state thereof. In addition to forming the one or more channels with the balloon-compressing pieces 212, the one or more balloon lobes 322 are configured to anchor the balloon catheter assembly in a patient's bladder.

As evidenced by FIGS. 3A-3D, as well as FIGS. 5A-5D, the balloon catheter assembly 300 typically includes a one-to-one-to-one correspondence of the one or more secondary drainage apertures 316, the one or more balloon-compressing pieces 212, and the one or more balloon-letting through holes 214 or the one or more balloon lobes 322. For example, the balloon catheter assembly of FIGS. 3A-3D includes two secondary drainage apertures 316A and 316B, two balloon-compressing pieces 212A and 212B, and two balloon-letting through holes 214A and 214B, which, in turn, provide two balloon lobes 322A and 322. In some embodiments, however, the balloon catheter assembly 300 can include fewer secondary drainage apertures 316 than one secondary drainage aperture for every balloon-compressing piece, balloon-letting through hole, or balloon lobe. That said, every balloon catheter assembly 300 should include at least one secondary drainage aperture, and it is beneficial in terms or draining residual urine through the balloon catheter assembly 300 to have one secondary drainage aperture for every channel formed over a balloon-compressing piece.

FIG. 4A is a schematic illustrating a first side view of a distal end portion of a balloon catheter assembly 400 with the balloon-manipulating device 200 configured as a balloon-shaping cap disposed over a balloon 320 in an uninflated state in accordance with some embodiments. FIG. 4B is a schematic illustrating the first side view of the distal end portion of the balloon catheter assembly 400 of FIG. 4A with the balloon-shaping cap disposed over the balloon 320 in an inflated state.

As shown, the balloon catheter assembly 400 includes the balloon-manipulating device 200 configured as a balloon-shaping cap having an opened proximal end and a closed distal end. The balloon-shaping cap, description for which is already set forth herein, can be disposed over the balloon 320 such that: i) one or more sidewall through holes in a proximal end portion of the tubular body 210 align with the one or more primary drainage apertures 314, and ii) a distal end portion of the tubular body 210 is adjacent the one or more secondary drainage apertures 316. Aside from the balloon-manipulating device 200 of FIGS. 4A and 4B being configured as a balloon-shaping cap, the balloon catheter assembly 400 shares the same features as the balloon catheter assembly 300, description for which is set forth herein.

Figure 5A:
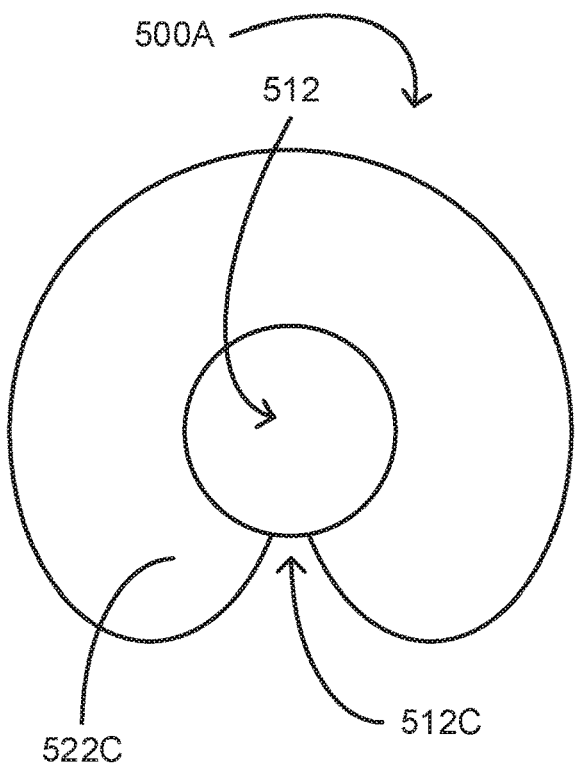
FIG. 5A is a schematic illustrating a distal end-on view of a balloon catheter assembly with a one-holed balloon-shaping sleeve disposed over a balloon in an inflated state in accordance with some embodiments.
Figure 5B:
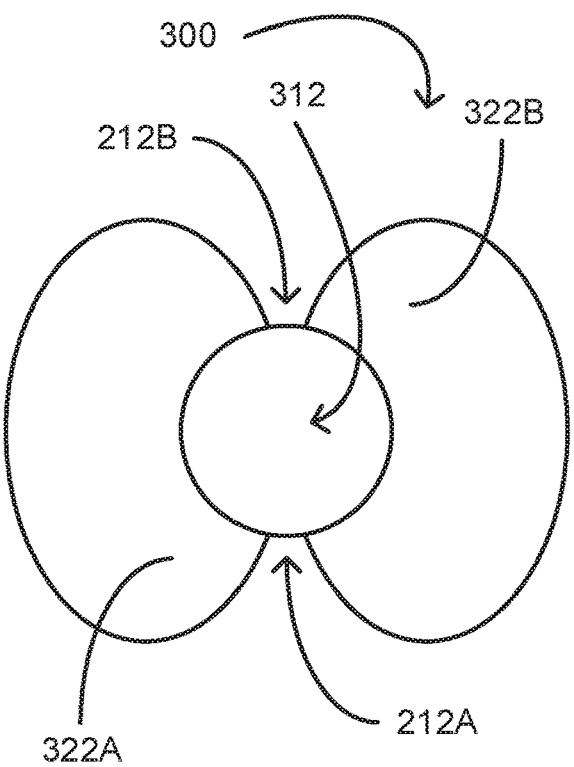
FIG. 5B is a schematic illustrating a distal end-on view of a balloon catheter assembly with a two-holed balloon-shaping sleeve disposed over a balloon in an inflated state in accordance with some embodiments.
Figure 5C:
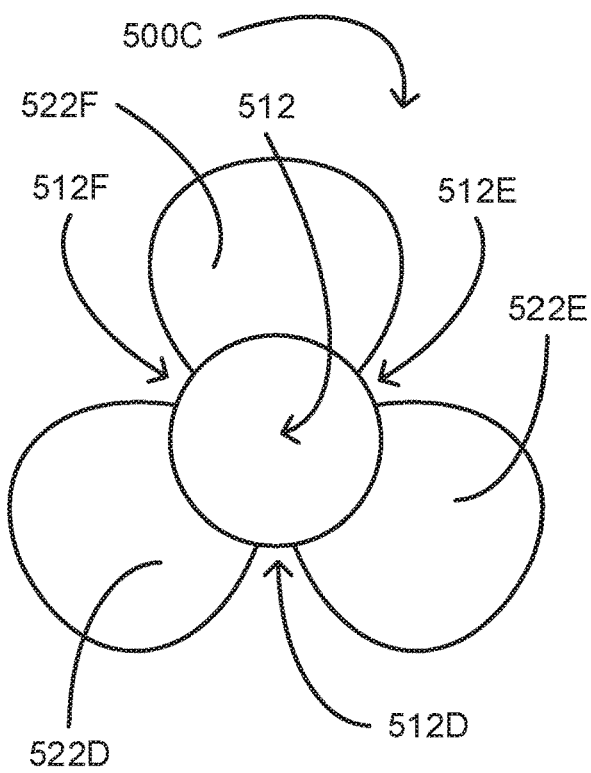
FIG. 5C is a schematic illustrating a distal end-on view of a balloon catheter assembly with a three-holed balloon-shaping sleeve disposed over a balloon in an inflated state in accordance with some embodiments.
Figure 5D:
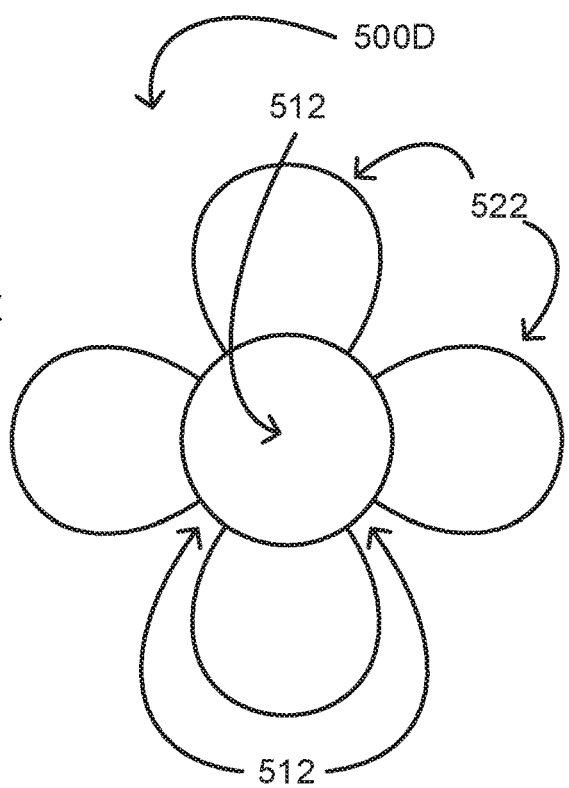
FIG. 5D is a schematic illustrating a distal end-on view of a balloon catheter assembly with a four-holed balloon-shaping sleeve disposed over a balloon in an inflated state in accordance with some embodiments.

FIG. 5A is a schematic illustrating an end-on view from a distal end 512 of a balloon catheter assembly 500A with a one-holed balloon-manipulating device 200 disposed over a balloon 520 in an inflated state in accordance with some embodiments. FIG. 5B is a schematic illustrating an end-on view from the distal end 312 of the balloon catheter assembly 300 with the two-holed balloon-manipulating device 200 disposed over the balloon 320 in an inflated state in accordance with some embodiments. FIG. 5C is a schematic illustrating an end-on view from the distal end 512 a balloon catheter assembly 500C with a three-holed balloon-manipulating device 200 disposed over the balloon 520 in an inflated state in accordance with some embodiments. FIG. 5D is a schematic illustrating an end-on view from the distal end 512 a balloon catheter assembly 500C with a four-holed balloon-manipulating device 200 disposed over the balloon 520 in an inflated state in accordance with some embodiments. While the balloon-manipulating device 200 is not expressly shown in any of FIGS. 5A-5D, a configuration for the balloon-manipulating device 200 of any of FIG. 5A, 5C, or 5D can be inferred by way of description for the balloon-manipulating device 200 of FIGS. 2, 3A-3D, 4A, and 4D and the relationship between FIG. 5B and FIGS. 3A-3D (e.g., the balloon-manipulating device 200 configured as a balloon-shaping sleeve) or FIG. 5B and FIGS. 4A and 4B (the balloon-manipulating device 200 configured as a balloon-shaping cap).

As shown in FIG. 5A, the balloon catheter assembly 500A includes a balloon-manipulating device 200 such as a balloon-manipulating sleeve or a balloon-manipulating cap including one balloon-compressing piece 512C and one balloon-letting through hole (not shown) resulting in one balloon lobe 522C when a balloon of the balloon catheter assembly 500A is in an inflated state thereof. Such a catheter assembly can include a secondary drainage aperture in a balloon-catheter shaft longitudinally aligned with a single channel formed along the balloon-compressing piece 512C and between opposing sides of the balloon lobe 522C. As such, the balloon catheter assembly 500A includes a one-to-one-to-one correspondence of the secondary drainage aperture, the balloon-compressing piece 512C, and the balloon-letting through hole or the balloon lobe 522C.

As shown in FIG. 5B, the balloon catheter assembly 300 includes the balloon-manipulating device 200 configured as either the balloon-manipulating sleeve or the balloon-manipulating cap, which includes two balloon-compressing pieces 212A and 212B and two balloon-letting through holes 214A and 214B resulting in two balloon lobes 322A and 322B when the balloon 320 of the balloon catheter assembly 300 is in the inflated state thereof. Such a catheter assembly can include two secondary drainage apertures 316A and 316B in the shaft 310, each secondary drainage aperture of which is longitudinally aligned with a channel formed along a respective balloon-compressing piece of the balloon-compressing pieces 212A and 212B and the balloon lobes 322A and 322B. As such, the balloon catheter assembly 300 includes a one-to-one-to-one correspondence of the secondary drainage apertures 316A and 316B, the balloon-compressing pieces 212A and 212B, and the balloon-letting through holes 214A and 214B or the balloon lobes 322A and 322B. In addition to the 2-fold rotational symmetry, or $C_2$ symmetry, about the longitudinal axis of the balloon-manipulating device 200 already set forth herein, the distal end portion of the catheter assembly 300, too, can have the foregoing rotational symmetry if the catheter assembly 300 includes the primary drainage apertures 314B in the shaft 310 opposite the primary drainage aperture 314A.

As shown in FIG. 5C, the balloon catheter assembly 500C includes a balloon-manipulating device 200 such as a balloon-manipulating sleeve or a balloon-manipulating cap including three balloon-compressing pieces 512D, 512E, and 512F and three balloon-letting through holes (not shown) resulting in three balloon lobes 522D, 522E, and 522F when a balloon of the balloon catheter assembly 500C is in an inflated state thereof. Such a catheter assembly can include three secondary drainage apertures in a balloon-catheter shaft, each secondary drainage aperture of which can be longitudinally aligned with a channel formed along a respective balloon-compressing piece of the balloon-compressing pieces 512D, 512E, and 512F and between two of the three balloon lobes 522D, 522E, and 522F. As such, the balloon catheter assembly 500C includes a one-to-one-to-one correspondence of the secondary drainage apertures, the balloon-compressing pieces 512D, 512E, and 512F, and the balloon-letting through holes or the balloon lobes 522D, 522E, and 522F. In addition to the 3-fold rotational symmetry, or $C_3$ symmetry, about the longitudinal axis of the balloon-manipulating device 200 already set forth herein, the distal end portion of the catheter assembly 500C, too, can have the foregoing rotational symmetry if the catheter assembly 500C includes primary drainage apertures in the balloon-catheter shaft longitudinally aligned with or offset from the secondary drainage apertures.

As shown in FIG. 5D, the balloon catheter assembly 500D includes a balloon-manipulating device 200 such as a balloon-manipulating sleeve or a balloon-manipulating cap including four balloon-compressing pieces 512 and four balloon-letting through holes (not shown) resulting in four balloon lobes 522 when a balloon of the balloon catheter assembly 500D is in an inflated state thereof. Such a catheter assembly can include four secondary drainage apertures in a balloon-catheter shaft, each secondary drainage aperture of which can be longitudinally aligned with a channel formed along a respective balloon-compressing piece of the balloon-compressing pieces 512 and between two of the four balloon lobes 522. As such, the balloon catheter assembly 500D includes a one-to-one-to-one correspondence of the secondary drainage apertures, the balloon-compressing pieces 512, and the balloon-letting through holes or the balloon lobes 522. In addition to the 4-fold rotational symmetry, or $C_4$ symmetry, about the longitudinal axis of the balloon-manipulating device 200 already set forth herein, the distal end portion of the catheter assembly 500D, too, can have the foregoing rotational symmetry if the catheter assembly 500D includes primary drainage apertures in the balloon-catheter shaft longitudinally aligned with or offset from the secondary drainage apertures.

In view of the foregoing, there is no particular limit on the number or arrangement of balloon-compressing pieces or the balloon-letting through holes for a balloon-manipulating device 200 such as the balloon-manipulating sleeve or the balloon-manipulating cap.

Figure 6A:
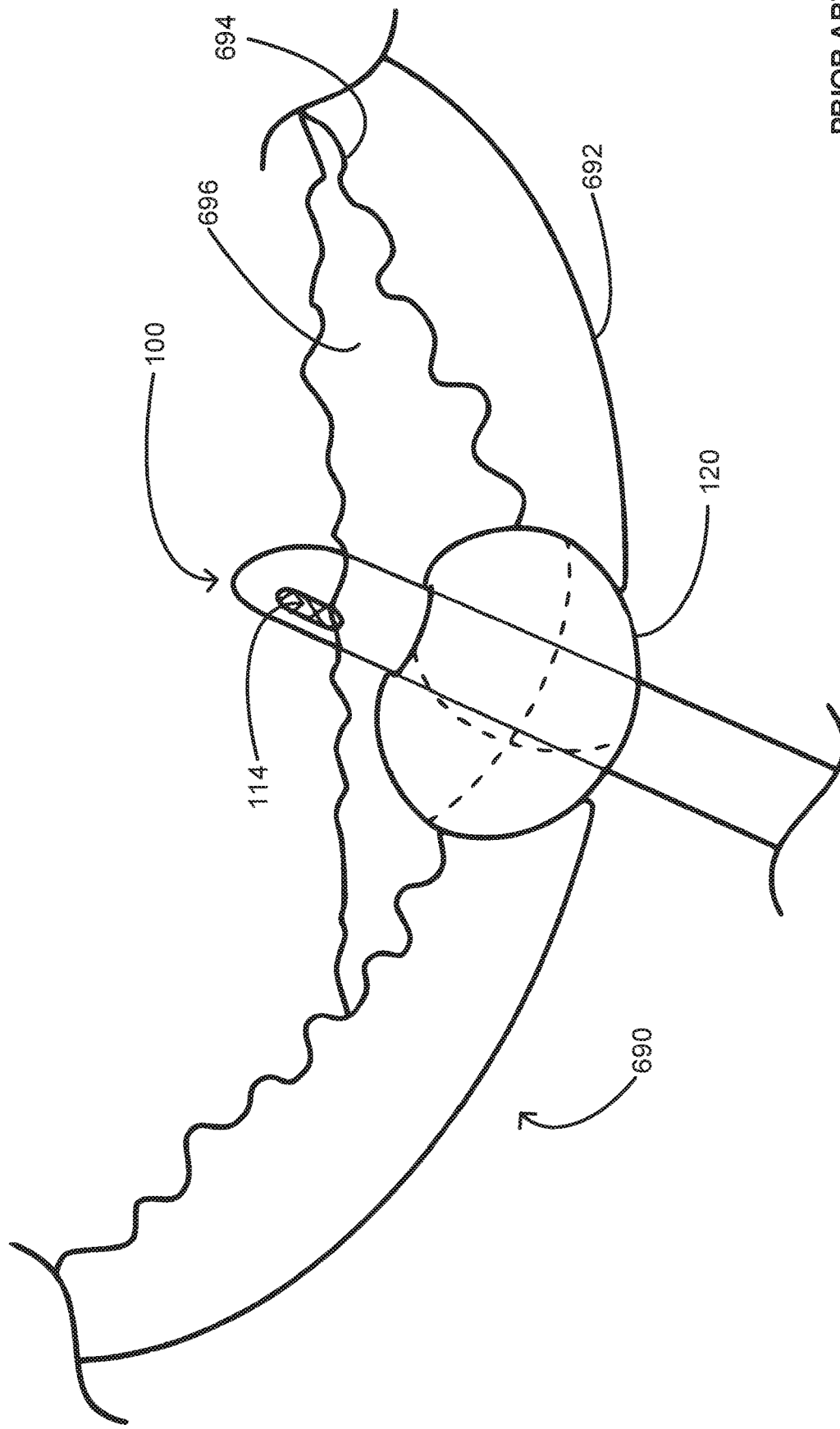
FIG. 6A is a schematic illustrating a conventional Foley catheter anchored in a bladder with a balloon in an inflated state.

FIG. 6A is a schematic illustrating the conventional Foley catheter 100 anchored in a bladder 690 with the balloon 120 in an inflated state.

As shown, the bladder 690 is formed by an interior bladder wall 694 and an exterior bladder wall 692. A volume of urine 696 is permitted to flow into the drainage aperture 114 and through the catheter 100. The volume of urine 696 is a residual volume of urine, much of which is below the drainage aperture 114 and, thus, cannot be fully drained. This residual volume of urine 696 can lead to increased rates of infection and discomfort in a patient if not removed.

Figure 6B:
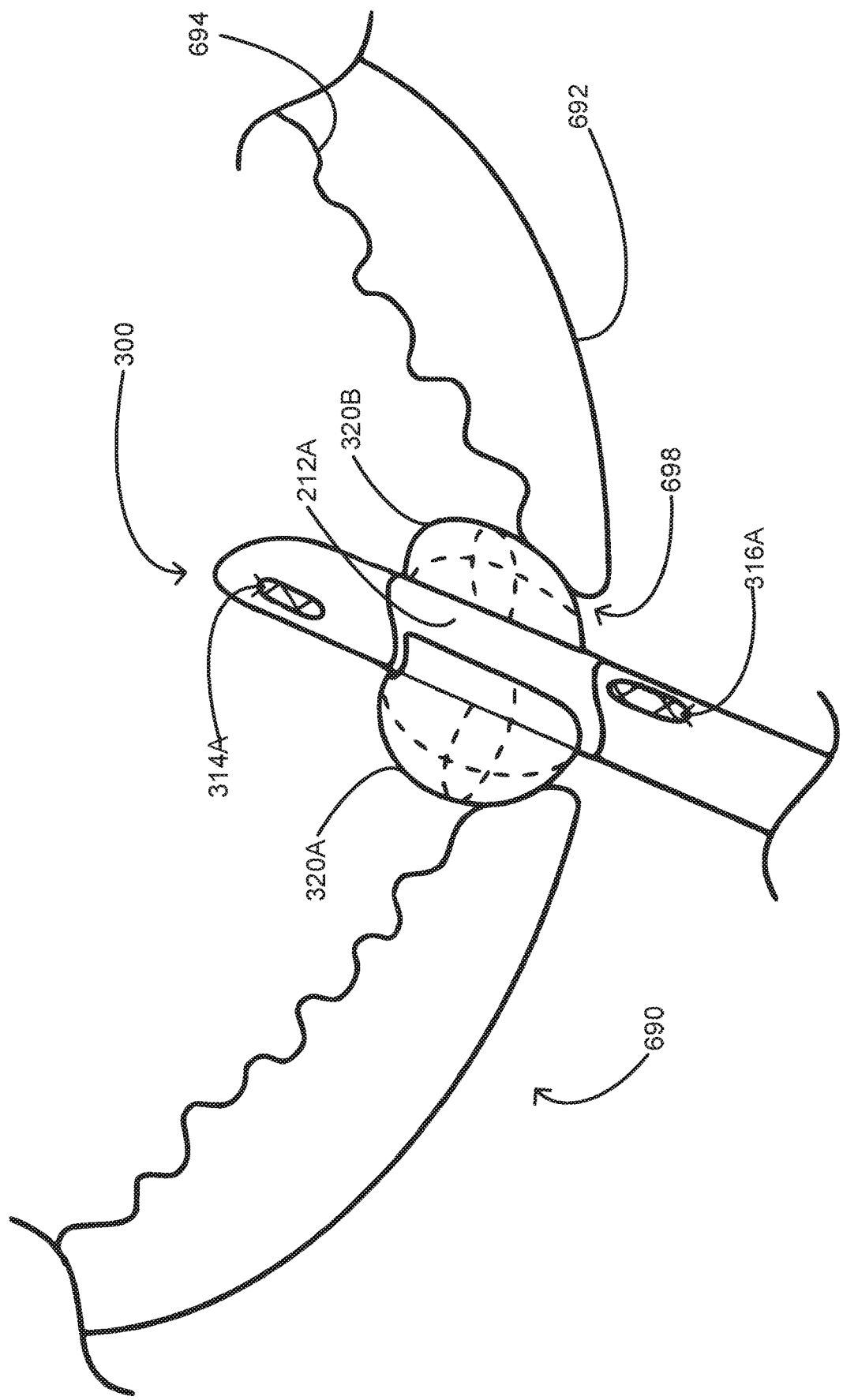
FIG. 6B is a schematic illustrating a balloon catheter assembly anchored in a bladder with a balloon in an inflated state shaped by a balloon-shaping sleeve disposed over the balloon in accordance with some embodiments.

FIG. 6B is a schematic illustrating the balloon catheter assembly 300 anchored in the bladder 690 with the balloon 320 in the inflated state shaped by the balloon-shaping sleeve disposed over the balloon 320 in accordance with some embodiments.

As shown, the balloon catheter assembly 300 is positioned in the bladder 690 with balloon lobes 320A and 320B sufficiently inflated to anchor the balloon catheter assembly 300 in the bladder 690. The primary drainage aperture 314A is configured to drain urine from the bladder 690, and the secondary drainage aperture 316A is configured to drain the residual volume of the urine 696 (see FIG. 6A) that does not flow into the primary drainage aperture 314A. The residual volume of the urine 696 can flow through the bladder neck 698, down the urethra (not shown), and into the additional drainage aperture 316A. As such, efficient drainage of fluids and debris from the bladder is accomplished by extending drainage apertures along a greater length of the shaft 310 of the balloon catheter assembly 300.

Shafts, catheter bodies, or catheters of balloon catheter assemblies such as the balloon catheter assembly 300 can be manufactured from natural rubber latex. Synthetic polyisoprene or silicone can also be used to prevent allergic reactions caused by certain protein(s) present in natural rubber latex. Conventional processes for making elastomeric articles such as the foregoing from natural or synthetic latex typically involve preparing a latex dispersion or emulsion, dipping a former in the shape of the article to be manufactured into the latex, and curing the latex while on the former. In the curing step, cross-linking or vulcanization through sulfur groups occurs between the polymer chains. After formation, some catheters are dipped in a coating solution so as to be slippery for insertion into the human body.

Balloons of balloon catheter assemblies such as the balloon catheter assembly 300 can be formed in a number of different ways, and any method of forming the balloon may be used. For example, a balloon can be formed by application of a pre-formed balloon component on an intermediate layer of latex. An additional layer (e.g., a "finish layer") can be applied over the pre-formed balloon component and, thus, forms part of the wall of the balloon.

Balloon-manipulating devices such as the balloon-manipulating device 200 can be manufactured as already set forth herein. Installation of such a balloon-manipulating device is effected by way of inserting a balloon-catheter shaft in the longitudinal hole of the balloon-manipulating device while aligning any tabs, notches, or sidewall through holes of the balloon-manipulating device with the primary and secondary drainage apertures.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A balloon-manipulating device for a balloon catheter, comprising:
 a tubular body including:
  a proximal end portion;
  a distal end portion;
  an open distal end forming a balloon-manipulating sleeve configured for inserting a balloon-catheter shaft therethrough, the balloon-manipulating sleeve including 2-fold rotational symmetry about a longitudinal axis of the balloon-manipulating sleeve; and
  a pair of tabs and a pair of cutouts, each tab of the pair of tabs extending from an opposite side of the distal end portion of the tubular body, and each cutout of the pair of cutouts in an opposite side of the proximal end portion of the tubular body, wherein the tubular body is seamless to withstand tensile stress imparted to the tubular body when inflating a balloon-catheter balloon under the balloon-manipulating sleeve;
 a longitudinal hole extending from an opened proximal end of the tubular body to at least the distal end portion of the tubular body, the longitudinal hole configured for inserting a balloon-catheter shaft in the longitudinal hole;
 one or more balloon-compressing pieces of a sidewall of the tubular body, each balloon-compressing piece configured for compressing a different portion of a balloon-catheter balloon when the balloon-manipulating device is disposed over the ballon-catheter balloon and the balloon-catheter balloon is in an inflated state thereof; and one or more balloon-letting through holes through the sidewall of the tubular body, each balloon-letting through hole configured for allowing therethrough a different portion of a balloon-catheter balloon when the balloon-manipulating device is disposed over the balloon-catheter balloon and the balloon-catheter balloon is in an inflated state thereof.

2. A balloon catheter assembly, comprising:
a balloon catheter including:
one or more primary drainage apertures in a distal end portion of a shaft of the balloon catheter;
one or more secondary drainage apertures in the distal end portion of the shaft, the one or more secondary drainage apertures closer to a proximal end portion of the shaft than the one or more primary drainage apertures; and
a balloon coupled to the shaft between the one or more primary drainage apertures and the one or more secondary drainage apertures, the balloon fluidly coupled to an inflation lumen extending through a length of the shaft configured for inflating the balloon; and
a balloon-manipulating device, including:
a tubular body disposed over the balloon, the tubular body including a proximal end portion adjacent the one or more primary drainage apertures and a distal end portion adjacent the one or more secondary drainage apertures;
one or more balloon-compressing pieces of a sidewall of the tubular body, each balloon-compressing piece configured for compressing a different portion of the balloon when the balloon is in an inflated state; and
one or more balloon-letting through holes through the sidewall of the tubular body, each balloon-letting through hole configured for allowing therethrough a different portion of the balloon when the balloon is in the inflated state.

3. The balloon catheter assembly of claim 2, wherein:
each different portion of the balloon compressed by the one or more balloon-compressing pieces forms a channel when the balloon is in the inflated state,
each different portion of the balloon let through the one or more balloon-letting through holes forms a balloon lobe when the balloon is in the inflated state, and
one or more balloon lobes are configured to anchor the balloon catheter assembly in a bladder of a patient, and one or more channels are configured to transport residual urine from the bladder, through a bladder neck, through a portion of a urethra, and to the one or more secondary drainage apertures for drainage of the residual urine.

4. The balloon catheter assembly of claim 2, wherein the balloon catheter assembly includes a one-to-one-to-one correspondence of the one or more secondary drainage apertures, the one or more balloon-compressing pieces, and the one or more balloon-letting through holes.

5. The balloon catheter assembly of claim 2, wherein the tubular body is seamless to withstand tensile stress imparted to the tubular body when the balloon is in the inflated state.

6. The balloon catheter assembly of claim 2, wherein:
the tubular body includes an opened proximal end and a closed distal end, thereby forming a balloon-manipulating cap, and
the balloon-manipulating cap includes one or more sidewall through holes in the distal end portion of the tubular body configured to align with the one or more primary drainage apertures.

7. The balloon catheter assembly of claim 2, wherein the tubular body includes an opened proximal end and an opened distal end, thereby forming a balloon-manipulating sleeve.

8. The balloon catheter assembly of claim 2, wherein the tubular body includes one or more tabs, one or more cutouts, or a combination thereof, each tab of the one or more tabs independently extending from the distal end portion or the proximal end portion of the tubular body, and each cutout of the one or more cutouts is independently in the distal end portion or the proximal end portion of the tubular body.

9. The balloon catheter assembly of claim 8, wherein:
the one or more tabs are circumferentially arranged around the distal end portion of the tubular body such that the one or more tabs alternate with the one or more primary drainage apertures, and
the one or more cutouts are circumferentially arranged around the proximal end portion of the tubular body such that the one or more cutouts align with the one or more secondary drainage apertures.

10. The balloon catheter assembly of claim 2, wherein the tubular body includes:
an opened proximal end and an opened distal end, thereby forming a balloon-manipulating sleeve; and
a pair of tabs extending from the distal end portion of the tubular body and a pair of cutouts in the proximal end portion of the tubular body.

11. The balloon catheter assembly of claim 10, wherein the balloon-manipulating device includes $C_2$ symmetry about a longitudinal axis of the balloon-manipulating device.

12. The balloon catheter assembly of claim 10, wherein:
the pair of tabs are circumferentially arranged around the distal end portion of the tubular body to include one primary drainage aperture between the pair of tabs or alternate with the one or more primary drainage apertures, and
the pair of cutouts are circumferentially arranged around the proximal end portion of the tubular body to align with the one or more secondary drainage apertures.

13. A balloon catheter assembly, comprising:
a balloon catheter, including:
one or two primary drainage apertures in a distal end portion of a shaft of the balloon catheter;
one or two secondary drainage apertures in the distal end portion of the shaft, the one or two secondary drainage apertures closer to a proximal end portion of the shaft than the one or two primary drainage apertures; and
a balloon coupled to the shaft between the one or two primary and secondary drainage apertures, the balloon fluidly coupled to an inflation lumen extending through a length of the shaft configured for inflating the balloon; and
a balloon-manipulating sleeve, including:
a tubular body disposed over the balloon, the tubular body including a proximal end portion adjacent the one or two primary drainage apertures and a distal end portion adjacent the one or two secondary drainage apertures;
one or two balloon-compressing pieces of a sidewall of the tubular body, each balloon-compressing piece configured for compressing a different portion of the balloon to form a corresponding channel when the balloon is in an inflated state; and
one or two balloon-letting through holes through the sidewall of the tubular body, each balloon-letting through hole configured for allowing therethrough a different portion of the balloon to form a corresponding balloon lobe when the balloon is in the inflated state, wherein one or two balloon lobes are configured to anchor the balloon catheter assembly in a bladder of a patient, and one or two channels are configured to transport residual urine from the bladder, through a bladder neck, through a portion of a urethra, and to the one or two secondary drainage apertures for drainage of the residual urine while the balloon catheter assembly is anchored in the bladder of the patient by the one or two balloon lobes.

14. The balloon catheter assembly of claim 13, wherein the balloon catheter assembly includes one primary drainage aperture and one secondary drainage aperture in the distal end portion of the shaft, one balloon-compressing piece of the sidewall of the tubular body, and one balloon-letting through hole through the sidewall of the tubular body.

15. The balloon catheter assembly of claim 13, wherein the balloon catheter assembly includes one primary drainage aperture and two secondary drainage apertures in the distal end portion of the shaft, two balloon-compressing pieces of the sidewall of the tubular body, and two balloon-letting through holes through the sidewall of the tubular body.

* * * * *